United States Patent [19]

Wolf et al.

[11] Patent Number: 4,767,416
[45] Date of Patent: Aug. 30, 1988

[54] SPRAY NOZZLE FOR SYRINGE

[75] Inventors: Stephen J. Wolf, Manville; James P. Dellas, East Brunswick, both of N.J.

[73] Assignee: Johnson & Johnson Patient Care, Inc., New Brunswick, N.J.

[21] Appl. No.: 936,534

[22] Filed: Dec. 1, 1986

[51] Int. Cl.⁴ ............................................. A61M 5/325
[52] U.S. Cl. ..................................... 604/239; 604/275
[58] Field of Search ........................ 604/239, 240–243, 604/310, 311, 283, 164, 165, 275, 279; 128/200.14, 200.22, 207.14

[56] References Cited

U.S. PATENT DOCUMENTS

| 3,491,757 | 1/1970 | Arce | 604/242 |
| 4,405,308 | 9/1983 | Jessup | 604/239 |
| 4,540,405 | 9/1985 | Miller et al. | 604/241 |
| 4,607,868 | 8/1986 | Harvey et al. | 604/243 |

Primary Examiner—John D. Yasko
Attorney, Agent, or Firm—Joseph F. Shirtz

[57] ABSTRACT

A spray syringe is disclosed which includes in combination a hypodermic syringe and a tubular member having a spray orifice at a distal tip. The tubular member is flexible permitting orientation of the spray orifice independent of the orientation of the syringe. The tubular member is sized such that the needle of the syringe is received within the bore in a fluid tight seal.

5 Claims, 1 Drawing Sheet

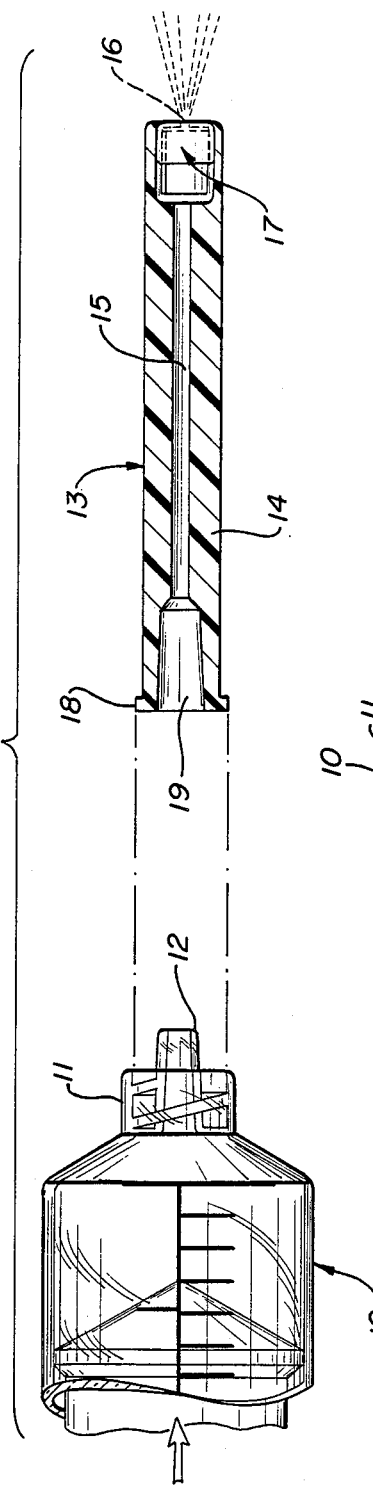

SPRAY NOZZLE FOR SYRINGE

FIELD OF INVENTION

This invention relates to liquid spray applicators and more particularly to a spray tip adapted for use with a hypodermic syringe.

BACKGROUND OF THE INVENTION

In certain medical procedures, it is necessary or desirable to apply therapeutic solutions to wound or surgical sites by spraying the solution gently onto the affected area. The application of anti-bacterial agents or wound healing accelerators in the treatment of burns, for example, is best accomplished by spraying solutions of the active agent in sterile distilled water or saline. In surgical procedures, hemostatic agents such as thrombin may be advantageously delivered by spraying a sterile aqueous solution of the agent onto the bleeding tissue.

The application of therapeutic solutions by spraying has heretofore been accomplished by means of pump sprayers not unlike those used for household products. For example, in the case of thrombin, a sterile solution is prepared for mixing freeze-dried thrombin powder with saline and transferring this solution to a pump-type sprayer for application to the treatment area. The pump-type sprayer has several shortcomings in such use, most notable being the difficulty of treating hard to reach areas, the uncertainty of applying a specific amount of solution to a defined area, and the waste of expensive solution not readily picked up by the dip tube of the sprayer when the liquid level is near the bottom of the container.

It is accordingly, an object of the present invention to provide a novel spray device which overcomes the disadvantages of the pump sprayer. It is a further object of the present invention to provide a spray device which is easy and convenient for the physician to use. It is a yet further object to provide a means for converting a standard hypodermic syringe into a spray device. These and other objects of the present invention will be apparent from the ensuing description and claims.

SUMMARY OF THE INVENTION

In accordance with the present invention, a spray nozzle comprising a tubular member terminating in a liquid spray orifice is provided for use with a conventional hypodermic syringe. In one embodiment, the spray nozzle is adapted for attachment directly to the luer fitting of the syringe in place of the hypodermic needle. In another embodiment, the spray nozzle is adapted to fit over a hypodermic needle which is attached to the luer fitting of the syringe. the length of the spray nozzle permits the spray to be directed to the treatment area, and an optional flexible coupling may be included to permit the direction of the spray tip to be controlled independently of the orientation of the syringe.

A spray nozzle of the present invention permits the syringe to be used as a liquid reservoir. The syringe is calibrated so that the therapeutic solution may be applied in precisely controlled volumes. The syringe may be repeatedly refilled if necessary, and when finally emptied very little solution remains in the syringe or spray nozzle.

DESCRIPTION OF DRAWINGS

FIG. 1 illustrates a spray nozzle to be secured directly to luer fitting of a syringe.

FIG. 2 illustrates a spray nozzle to be secured over a hypodermic needle on the syringe.

FIG. 3 illustrates a spray nozzle which includes a flexible coupling between the spray tip and the syringe.

DESCRIPTION OF INVENTION

The spray nozzle for use with a syringe in accordance with the present invention comprises any elongated tubular member having a liquid spray tip orifice at one end and being adapted for attachment to the liquid discharge port of the syringe at the other end. The spray nozzle may attach directly to the luer fitting of the syringe, or may be adapted to fit over and attach to a hypodermic needle secured to the luer fitting. In either event, the tubular member terminates in a liquid spray tip orifice through which the contents of the syringe may be discharged. The spray tip may be of any convention design which is commonly used in liquid spray dispensers for both medical and household products.

Referring now to FIG. 1, there is illustrated syringe 10 having luer fitting 11 and a liquid discharge port 12. The spray tip of the present invention, indicated generally as 13, consists of an elongated tubular member 14 having internal conduit 15 which terminates at the end distal from the syringe in orifice 16 which is the discharge orifice of the spray tip indicated generally as 17. The proximal end of the spray nozzle is provided with luer fitting 18 which attaches directly to the syringe. Discharge port 12 of the syringe is received by chamber 19 of the spray nozzle in a fluid tight seal to prevent back flow and leakage of the liquid discharged from the syringe.

FIG. 2 illustrates another embodiment of the present invention wherein hypodermic needle 21 is attached to luer fitting 11 of syringe 10 and spray nozzle 20 is adapted to fit over and enclose the hypodermic needle. In the illustrated embodiment, conduit 25 of the spray nozzle 20 is tapered from a major diameter 26 at the end proximal to the syringe, which diameter is sufficient to receive the luer fitting 24 of the needle, to a reduced diameter 27 adjacent the tip of the needle. The spray nozzle engages the tip of the needle in area 27 of reduced diameter whereby a liquid tight seal is formed to prevent liquid discharged from end 28 of the hypodermic needle from leaking back along the barrel of the needle. Conduit 29 leads from needle tip 28 to the spray nozzle indicated generally as 22 whereupon liquid discharged from the tip of the needle is directed to spray orifice 23.

FIG. 3 illustrates a further modification of the spray nozzle illustrated in FIG. 2. In particular, distal end 30 of spray nozzle 20 is provided with means to secure flexible conduit 31 which may be, for example, a length of Tygon or silicone tubing. In this embodiment, the spray tip indicated generally as 33 is secured to the opposite end of the flexible tubing, and the liquid spray exiting from spray tip orifice 34 may be directed independently of the orientation of the syringe. The length of the flexible tubing may be as little as about 1 cm to provide directional flexibility, or as much as about 50 cm for gastrointestinal procedures wherein the spray tip may be introduced into the esophagus or stomach by means of a flexible esophageal probe.

The embodiment of FIG. 3 is particularly preferred for many surgical procedures where access to the treatment site may be difficult. In thoracic surgical for example, the embodiment of FIG. 3 permits therapeutic solutions such as coagulants or adhesion preventors to be applied to organs deep within the body cavity of the patient. The embodiment of FIGS. 1 or 2 on the other hand, are preferred for the application of liquid sprays to surface wounds, oral cavities and other easily accessed areas.

The embodiments of FIGS. 2 and 3 are particularly preferred where the liquid or one component of the liquid to be applied is supplied in a container having a needle septum. In such a system, the syringe is filled by inserting the needle into the container, and the spray nozzle is easily attached to the filled syringe directly over the needle. The syringe may be conveniently refilled by simply removing the spray nozzle, again inserting the needle into the container, and then reattaching the spray nozzle.

The combination of a spray nozzle and a hypodermic syringe in accordance with the present invention provides the medical practitioner with a new and useful device for applying therapeutic solutions in a fine mist or spray. The present invention allows the practitioner to apply precisely controlled volumes of solutions to very specific areas with a minimum of wasted time or material.

The specific embodiments described herein and illustrated in FIGS. 1-3 are for purposes of illustration only, and many variations thereof will be apparent to those skilled in the art. The present invention is accordingly not limited except as defined in the following claims.

We claim:

1. A spray syringe comprising, in combination, a hypodermic syringe having a luer fitting and a tubular member terminating in a liquid spray orifice, means for attaching said tubular member directly to said fitting and said tubular member includes a flexible conduit section between said fitting and said liquid spray orifice.

2. A spray syringe comprising, in combination, a hypodermic syringe having a hypodermic needle secured thereto, a tubular member enclosing said hypodermic needle and terminating in a liquid spray orifice, and means for securing said tubular member to said hypodermic needle and wherein said tubular member has an inside bore sized to engage the hypodermic needle adjacent the tip thereof in a fluid tight seal, whereby liquid discharged from the tip of said needle is prevented from flowing between said needle and said tubular member.

3. A spray syringe of claim 2 wherein said tubular member includes a flexible conduit section intermediate the tip of said hypodermic needle and said spray orifice.

4. A spray nozzle for use with a hypodermic syringe having a hypodermic needle attached thereto, said spray nozzle comprising an elongated tubular member adapted to enclose said hypodermic needle and engage said hypodermic needle in a fluid tight seal adjacent the tip of said needle, said tubular member extending beyond the tip of said hypodermic needle and terminating in a liquid spray orifice.

5. A spray nozzle of claim 4 wherein said tubular member includes a flexible conduit section intermediate the tip of said hypodermic needle and said spray orifice.

* * * * *